(12) United States Patent
Shepard

(10) Patent No.: US 6,761,739 B2
(45) Date of Patent: Jul. 13, 2004

(54) CORTICAL AND CANCELLOUS ALLOGRAFT SPACER

(75) Inventor: Yolanda Denise Shepard, Parlin, NJ (US)

(73) Assignee: Musculoskeletal Transplant Foundation, Edison, NJ (US)

( * ) Notice: Subject to any disclaimer, the term of this patent is extended or adjusted under 35 U.S.C. 154(b) by 0 days.

(21) Appl. No.: 10/302,895

(22) Filed: Nov. 25, 2002

(65) Prior Publication Data

US 2004/0102850 A1 May 27, 2004

(51) Int. Cl.$^7$ .............................. A61F 2/44; A61F 2/28
(52) U.S. Cl. .............................. 623/17.16; 623/23.51; 623/623; 623/23.61
(58) Field of Search .............................. 623/16.11, 17.11, 623/17.15, 17.16, 23.51, 23.61, 23.75; 606/61

(56) References Cited

U.S. PATENT DOCUMENTS

| | | | |
|---|---|---|---|
| 4,950,296 A | | 8/1990 | McIntyre |
| 5,766,618 A | * | 6/1998 | Laurencin et al. ........... 424/426 |
| 5,972,368 A | | 10/1999 | McKay |
| 6,033,438 A | * | 3/2000 | Bianchi et al. ............... 623/17 |
| 6,037,519 A | * | 3/2000 | McKay ........................ 623/16 |
| 6,136,029 A | * | 10/2000 | Johnson et al. .............. 623/16 |
| 6,187,329 B1 | * | 2/2001 | Agrawal et al. ............ 424/426 |
| 6,200,347 B1 | * | 3/2001 | Anderson et al. .......... 623/16.11 |
| 6,294,187 B1 | | 9/2001 | Boyce et al. |
| 6,379,385 B1 | | 4/2002 | Kalas et al. |
| 6,387,130 B1 | * | 5/2002 | Stone et al. .............. 623/17.16 |
| 6,398,811 B1 | * | 6/2002 | McKay .................... 623/17.16 |
| 6,458,158 B1 | * | 10/2002 | Anderson et al. ........ 623/16.11 |
| 2001/0041941 A1 | * | 11/2001 | Boyer, II et al. ........ 623/23.52 |
| 2002/0029084 A1 | * | 3/2002 | Paul et al. ............... 623/23.63 |
| 2003/0036800 A1 | * | 2/2003 | Meredith ................. 623/23.63 |
| 2003/0105528 A1 | * | 6/2003 | Shimp et al. ............ 623/17.16 |

FOREIGN PATENT DOCUMENTS

| | | |
|---|---|---|
| WO | WO 02/07654 A2 | 1/2002 |
| WO | WO 02/24122 A2 | 3/2002 |

* cited by examiner

Primary Examiner—Eduardo C. Robert
Assistant Examiner—Anuradha Ramana
(74) Attorney, Agent, or Firm—John S. Hale; Gipple & Hale

(57) ABSTRACT

A sterile composite bone graft for use in implants comprising an I beam cortical bone load bearing member upon which is mounted a trapezoidal shaped cancellous member. The allograft cancellous bone member defines tapered side walls, a flat proximal end wall and a flat distal end wall and a channel into the body leading from the front wall to the end wall. The I beam cortical member has a front section with a flat rear surface. A rectangular support bar extends from the flat rear surface to the flat rear wall of the rear section forming a connecting bar which fits into the channel cut into the cancellous member body. The I beam cortical member support bar and the channel of the cancellous member mate together to hold both component members in stable relationship. Pins may be mounted in both members on opposite sides of the members interface.

53 Claims, 2 Drawing Sheets

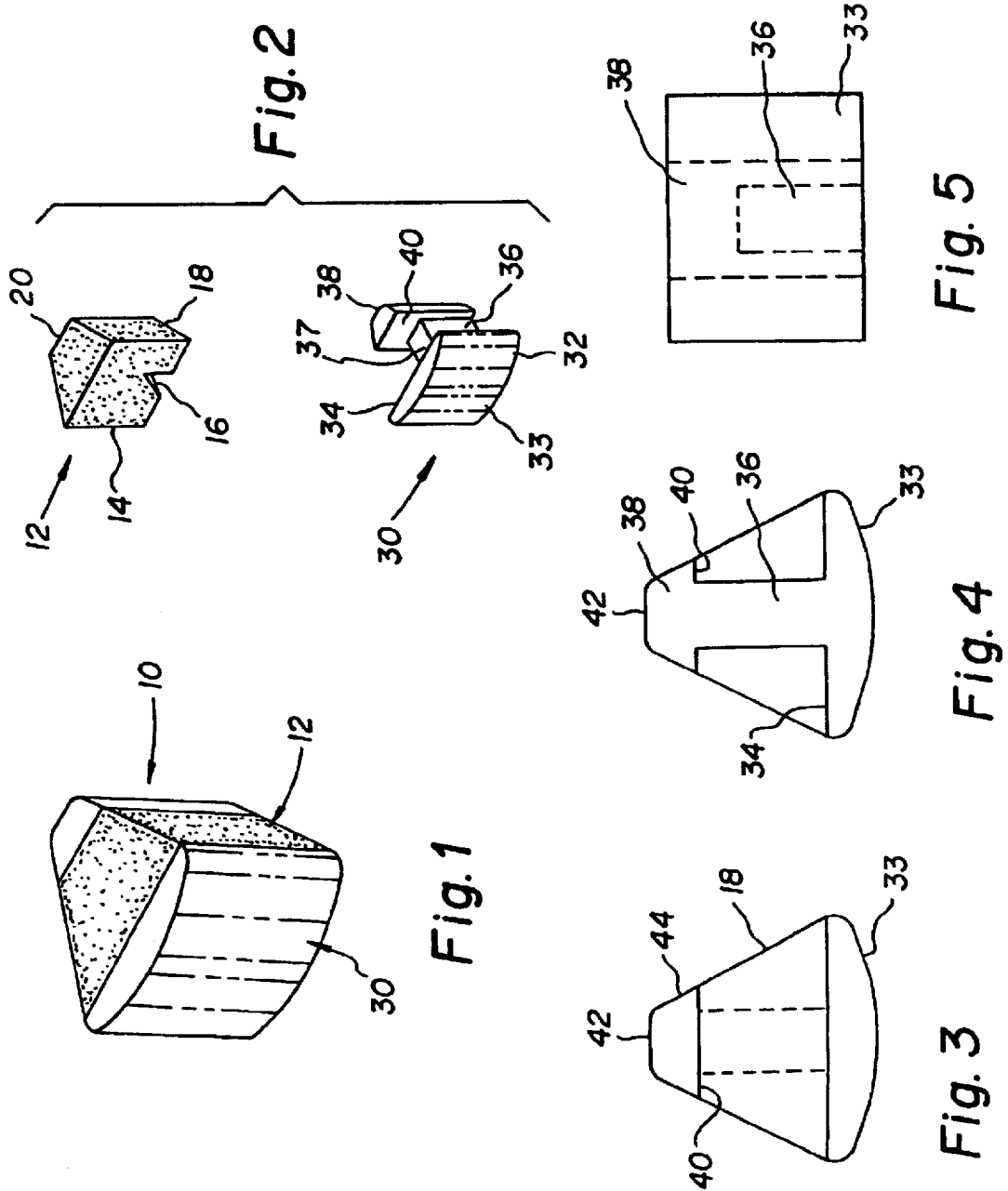

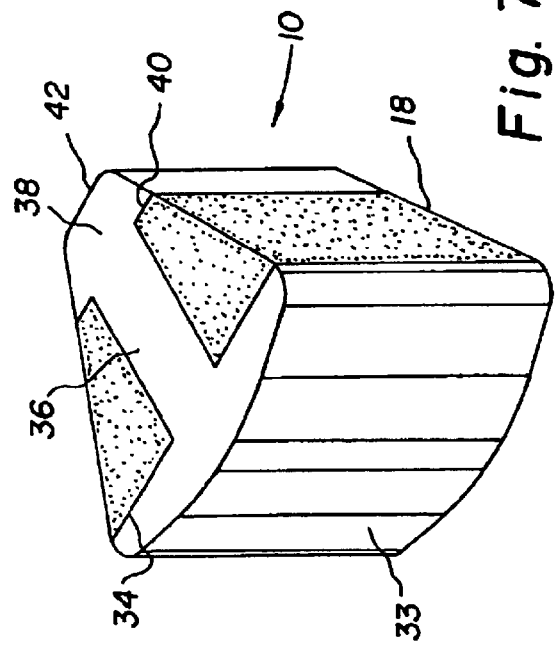
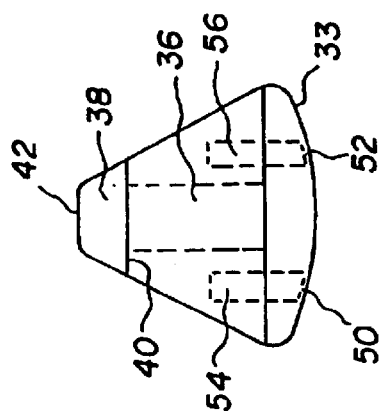
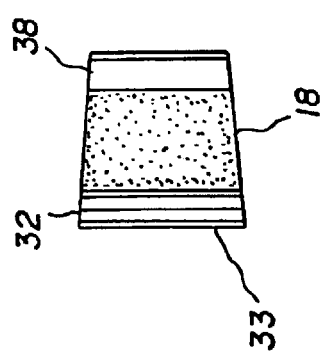
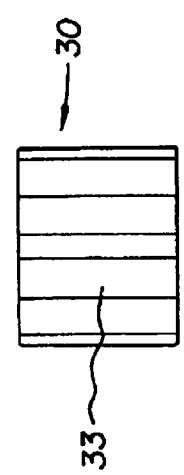

CORTICAL AND CANCELLOUS ALLOGRAFT SPACER

RELATED APPLICATION

There are no related applications.

1. Field of Invention

The present invention is generally directed toward a surgical implant product and more specifically is a shaped allograft cortical cancellous bone block implant for the fusion of vertebral bones which is introduced between two vertebral bones to be fused.

2. Background of the Invention

The use of substitute bone tissue dates back around 1800. Since that time research efforts have been undertaken toward the use of materials which are close to bone in composition to facilitate integration of bone grafts. Developments have taken place in the use of grafts to use materials such as corals, hydroxyapatites, ceramics or synthetic materials such as biodegradable polymer materials. Surgical implants should be designed to be biocompatible in order to successfully perform their intended function. Biocompatibility may be defined as the characteristic of an implant acting in such a way as to allow its therapeutic function to be manifested without secondary adverse affects such as toxicity, foreign body reaction or cellular disruption.

Human allograft tissue is widely used in orthopaedic, neuro-, maxillofacial, podiatric and dental surgery. The tissue is valuable because it is biocompatible, strong, biointegrates in time with the recipient patient's tissue and can be shaped either by the surgeon to fit the specific surgical defect or shaped commercially in a manufacturing environment. Contrasted to most synthetic absorbable or nonabsorbable polymers or metals, allograft tissue integrates with the surrounding tissues.

Allograft bone is a logical substitute for autologous bone. It is readily available and precludes the surgical complications and patient morbidity associated with obtaining autologous bone as noted above. Allograft bone is essentially a collagen fiber reinforced hydroxyapatite matrix containing active bone morphogenic proteins (BMP) and can be provided in a sterile form. The demineralized form of allograft bone is naturally both osteoinductive and osteoconductive. The demineralized allograft bone tissue is fully incorporated in the patient's tissue by a well established biological mechanism. It has been used for many years in bone surgery to fill the osseous defects previously discussed.

Allograft bone occurs in two basic forms; cancellous and cortical. The cancellous bone includes void areas with the collagen fiber component contributing in part to torsional and tensile strength. The less dense cancellous bone provides an excellent matrix for rapid bone regeneration and repair.

Many devices of varying shapes and forms are fabricated from allograft cortical tissue by machining. Surgical implants such as pins, rods, screws, anchors, plates, intervertebral spacers and the like have been made and used successfully in human surgery. These pre-engineered shapes are used by the surgeon in surgery to restore defects in bone to the bone's original anatomical shape.

Injury or disease processes to the head, neck, or shoulders can cause abnormal forces to be applied on the cervical vertebra. Arthritis, motion induced "whiplash", or other trauma create this malfunction. This situation is often treated surgically by a procedure intended to fuse the two adjacent cervical or spinal vertebrae to each other. Such fusion relieves the pressure the partially displaced vertebrae place on the adjacent spinal nerves.

Many surgical devices have been developed and used successfully to immobilize and fuse the misaligned vertebrae. Metal plates screwed into the adjacent vertebrae work well, but after some time post-operatively, the stress rise occurring at the screw position causes erosion of the bone and resultant slipping. This has been improved by placing load-bearing spacers between the two (or more) misaligned vertebrae. The spacer is both load-bearing and of a material which will induce, or at least support, fusion between the vertebrae.

Removal of damaged or diseased discs, restoration of disc space height and fusion of adjacent vertebrae to treat chronic back pain and other ailments are known medical techniques. Implants such as intervertebral spacers are often implanted in the disc space engaging the vertebrae to maintain or reestablish disc space height after removal of all or a portion of the disc. The spacers are formed of a variety of both resorbable and non-resorbable materials, including, for example, titanium, surgical steel, polymers, composites and bone. It is currently considered desirable to promote fusion between the vertebral bodies that are adjacent to the damaged or diseased discs. Typically, an osteogenic material is combined with a spacer and inserted in the disc space to facilitate and promote bone growth. While the selection of the implant configuration and composition can depend upon a variety of considerations, it is often desirable to select a resorbable material than does not shield the bone ingrowth. Bone and bone-derived components can provide suitable material to prepare the implants. However, bone material and in particular cortical bone acceptable for use in implants is a scarce resource, being derived from limited number of human tissue donor resources.

Suitable bone or bone-derived material for use in implants, in general, is almost exclusively obtained from allograft and xenograft sources, both of which come from a limited supply. Since intervertebral spacers must withstand the compressive loads exerted by the spine, these implants are often cortical bone which has the mechanical strength suitable for use in any region of the spine. Cortical spacers are often shaped from cortical long bones, which are primarily found in the lower limbs and include, for example, femur, fibula, and the tibia bones. However, these long bones make up only a fraction of the available bone source. Cancellous bone, because of its superior osteoinductive properties, would be desirable to sue in the spinal implant. However, the lower mechanical strength of cancellous bone prohibits its use in many surgical applications. Thus, sources of bone suitable for structural intervertebral spacers are extremely limited. The scarcity of desired donor bone makes it difficult to provide implants having the desired size and configuration for implantation between vertebrae, which can require relatively large implants. It is further anticipated that as the population ages there will be an increased need for correction for spinal deformities and a concomitant increase in the demand for bone-derived components. Therefore, these structural bone portions must be conserved and used efficiently to provide implants. The scarcity of suitable bone material has also hindered efforts to design and manufacture varying configurations of suitable implants for arthodesis of the spine. Further, various implant configurations have not been physiologically possible to obtain given the structural and geometrical constraints of available donor bone.

One known treatment for fusing two vertebrae is the insertion of a suitably shaped dowel into a prepared cylindrical cavity which reaches the two vertebrae to be fused. The dowel used is preshaped bone or allograft bone.

A number of allograft bone spacers have been used in surgery as spacers. They are commonly identified with a letter designation as follows: an ACF spacer constructed as a cortical bone cross section, shaped like a washer, with teeth to discourage graft explusion and an axial center hole; a VG3 cervical spacer constructed with two ramp shaped cortical plates held together with cortical pins, the top and bottom surfaces being ridged to discourage graft expulsion; an ICW spacer constructed with an elongated "C" spaced cortical portion with a cancellous inside to allow rapid ingrowth (slice of iliac crest) and a SBS spacer constructed with a single piece cortical member with serrated top and bottom surfaces and an axial center hole.

The ICW (iliac crest wedge) has been used for a long time for cervical spine fusion and has a total load bearing force around 4500 Newtons. Testing has shown that cervical vertebrae fail in compression at about 2000 Newtons. The ICW spacer suffers from high unit variability because of its natural, anatomic variations.

U.S. Pat. No. 5,972,368 issued on Oct. 26, 1999 discloses the use of cortical constructs (e.g. a cortical dowel for spinal fusion) which are cleaned to remove all of the cellular material, fat, free collagen and non-collagenous protein leaving structural or bound collagen which is associated with bone mineral to form the trabecular struts of bone. The shaped bone is processed to remove associated non-coluagenous bone proteins while maintaining native bound collagen materials and naturally associated bone minerals. The surface of a machined cortical bone is characterized by a wide variety of openings resulting from exposure by the machining process of the Haversian canals present throughout cortical bone. These canals serve to transport fluids throughout the bone to facilitate the biochemical processes that occur at variable angles and depths within the bone.

An attempt to solve the increasing bone supply problems using a combined cortical and cancellous bone block is shown in U.S. Pat. No. 4,950,296 issued Aug. 21, 1990 which uses a cubically configured cortical shell defining a through going internal cavity and a cancellous plug fitted into the cavity so that the end surfaces of the cancellous plug are exposed. Another reference, WIPO Patent Publication Number WO 02/24122 A2, published Mar. 28, 2002 owned by SDGI Holdings Inc. show various intervertebral spacers formed of cortical and cancellous bone composites such as sandwiches, with intersecting ribs or rods.

U.S. Pat. No. 6,294,187 issued Sep. 25, 2001 is directed toward an shaped osteimplant of compressed bone particles. The shaped implant is disc shaped and has a number of holes drilled therein for macroporosity. The holes can be filled with an osteogenic putty material.

Conversely, WIPO Patent Publication Number WO 02/07654 A2, published Jan. 31, 2002 discloses intervertebral spacers formed of dense cancellous human or animal bone. In one embodiment, a cortical rod or cortical rods are placed in bores cut through a cancellous bone block to provide load bearing strength with the ends of the rods being exposed on both sides of the cancellous bone block. Another embodiment shows a "C" shaped cortical block with a cancellous plug inserted into the recess of the "C" to form a rectangular spacer. A pin is inserted through a bore cut through the legs of the "C" block and through the cancellous plug to keep the cancellous plug positioned with the recess of the cortical component. U.S. Pat. No. 6,379,385 issued Apr. 30, 2002 also discloses the use of a cancellous block having a plurality of cortical rods mounted in through going bores cut through the bone block. In another embodiment, a X-shaped cortical support member is mounted therein to provide structured strength to the composite implant.

Consequently, there is a need for a spacer which should have with a load bearing compressive strength of 1000 to 5000 Newtons with a compressive load to be a minimum of 3000 Newtons as a safety factor. There is also a need to have a zone of cancellous bone immediately adjacent to the load bearing cortical zone to permit rapid ingrowth of a patient's own new bone.

SUMMARY OF THE INVENTION

The composite allograft cervical fusion spacer is directed toward a two piece, mated bone fusion spacer constructed with one component member of load bearing material preferably cortical bone and the other component member made of cancellous bone for use in orthopedic surgical procedures. The cortical bone member defines a modified I beam shape with front and rear load engaging sections with the cancellous component member having a trapezoidal shape with a center channel cut therethrough to form a block C cross section. The center channel fits over the connector bar that forms the mid section of the cortical member connecting the front and rear load engaging sections. If desired, a plurality of angled bores are cut into or through both members to hold pins which are inserted through the head piece of the cortical member and the body of the cancellous member along opposite sides of the center channel to limit axial and lateral movement.

It is an object of the invention to use a bone construction geometry to provide a composite bone spacer of cancellous and cortical bone components having performance characteristics that meet or exceed conventional spinal fusion requirements.

It is another object of the invention to utilize a shaped cortical cancellous bone implant spacer which provides the mechanical strength characteristics that can withstand compression forces and provide overall strength and durability to the structure.

It is still another object of the invention to provide a spinal fusion implant spacer which uses a load bearing component member to take up the high forces which can arise between two vertebral bodies and a relatively porous cancellous component member to accelerate the healing process.

It is yet another object of the invention to provide a pre-machined shaped allograft bone implant which can be easily inserted between the vertebrae of a patient to effectively promote new bone growth and accelerate healing.

It is also an object of the invention to create a sterile bone fusion implant, which is sterile and which can be easily handled by the physician during surgery which eliminates or significantly reduces the physician from having to carve or modify the respective bone blocks.

These and other objects, advantages, and novel features of the present invention will become apparent when considered with the teachings contained in the detailed disclosure. This disclosure, along with the accompanying drawings, and description, constitutes a part of this specification and illustrates embodiments of the invention which serve to explain the principles of the invention.

BRIEF DESCRIPTION OF THE DRAWINGS

FIG. 1 is a perspective view of the inventive composite cortical and cancellous bone implant;

FIG. 2 is an exploded perspective view of the implant of FIG. 1;

FIG. 3 is a top plan view of the implant of FIG. 1;

FIG. 4 is a bottom plan view of the implant of FIG. 1;

FIG. 5 is a front elevational view of the cortical I beam component of FIG. 1 showing the mid section and rear section in phantom;

FIG. 6 is a side elevational view of the implant of FIG. 1;

FIG. 7 is an enlarged perspective view of the implant shown in FIG. 4;

FIG. 8 is a front elevational view of the implant of FIG. 7; and

FIG. 9 is a top plan view of an alternate embodiment of the implant of FIG. 1 showing the bores in phantom.

DETAILED DESCRIPTION OF THE INVENTION

The preferred embodiment and best mode of the present invention is shown in FIGS. 1 through 6. The composite bone implant block 10 is shown in FIG. 1 in accordance with the present invention.

The composite cortical cancellous intervertebral spacer 10 is preferably constructed with a first component member 12 of denser cancellous bone taken from donors which are preferably age 45 or less, cut into a trapezoidal shape. This component accounts for a large portion of the graft and provides a large area for bone fusion to occur. The component has a flat planar front end surface 14 and a channel 16 cut into the interior of the cancellous component body. The channel 16 runs from the front to back of the component member forming a rectangular shaped channel which is adapted to fit over the mid-section 36 of the cortical component member 30. The cancellous bone is harvested from a bone such as a tibia, humerus, patella, calcareous or femur. The side walls 18 of the cancellous member 12 are tapered or angled into a planar rear wall surface 20. The cancellous member 12 when implanted in the patient's body encourages tissue growth, vascularation and deposition of new bone.

The cortical cancellous bone block 10 has an I beam shaped cortical component member 30 with a distal section 32 having an arcuate outer surface 33 and a planar inner surface 34, a rectangularly shaped mid-section support or cross bar 36 which extends outward from the planar surface 34 and engages a front section 38. The planar top and bottom surface of the distal section 32 and front section 34 preferably form planes which are angled from the rear to the front from 3° to 5°, preferably 4°. The cross bar 36 is configured to seat in channel 16 of cancellous component member 12 and mate the two components together. The rear wall 40 of the front section 38 is planed and forms a stop for the rear end wall 20 of the cancellous component member 12. The front wall 42 is also planar with rounded corners 44. The cortical member 30 has superior wall strength for support between load bearing body structures such as vertebrae. When the composite assembly is lyophilized, the pieces shrink with the cortical bone shrinking about 3% and the cancellous bone shrinking a greater amount ranging from 4% to 8%. Thus, the support cross bar 36 will fit into channel 16 to hold the two components together in a mated relationship with the height of rear section 32 and front section 38 being about the same or of a slightly greater height than the height of the cancellous member 12 so that rear section 32 and front section 38 bear the load from the vertebrae. The cortical or load bearing member 30 has superior wall strength for support between load bearing body structures such as vertebrae and has a compressive load in excess of 1000 Newtons. The composite bone block body 10 height measured, can range from 5–12 mm preferably 10 mm depending upon patient needs with a corresponding length ranging from 10 to 13 mm, preferably 12 mm with a width as measured at the largest portion of the tapered body ranging from 12 mm to 18 mm preferably 16 mm, again depending upon surgeon preference and the size of the fusion block which will be used on the individual patient. The channel 16 is preferably 4 mm wide and 4 mm in depth with a length of 8 mm.

If desired, pins 50 and 52 can be inserted in a blind bores 54 and 56 cut in both component members 12 and 30 to increase stability to the graft. The pins 50 and 52 are preferably constructed of cortical bone but can be constructed from any bio-compatible material having the necessary strength requirements including metals, plastics compositions and the like and are friction fit in the respective bores 54 and 56. The cortical component 30 is mated to the cancellous component 12 with the support cross bar 36 having an upper planar surface 37 being adjacent the bottom of the channel 16 of the cancellous component 12. The cortical or load bearing component bears not only a compressive load but also serves as an impaction surface. Thus, the surgeon can tap on the anterior impaction surface 33 of the cortical member 30 with a hammer to impact the graft without damaging the more brittle cancellous portion of the graft.

While this operation has been discussed in terms of using the preferred embodiment, namely, allograft bone, alternative sources of the components of the bone blocks may be substituted. These alternative sources may include xenograft bone or synthetic graft materials. With any of these alternatives, the bone blocks may be shaped as described above. The devices provide the surgeon with a graft that has the combined and best characteristics of both cortical and cancellous bone materials.

The cancellous component can be partially or fully demineralized bone and the load bearing component can be formed of partially demineralized or mineralized bone, load bearing ceramic or biocompatible plastic.

The spacers of the present invention were prepared by machining cancellous bone from donors, preferably under 45 years of age which have a denser cancellous structure. Suitable bones which can be used are calcareous, patella, femoral head, long bone condyles and talus. Cortical bone was prepared by machining and was taken from any acceptable donor age. Suitable bones are the radius, ulna, femur, tibia, humerus and the talus.

The unique features of allograft bone that make it desirable as a surgical material are, its ability to slowly resorb and be integrated into the space it occupies while allowing the bodies own healing mechanism to restore the repairing bone to its natural shape and function by a mechanism known in the art as creeping substitution.

It is well known that bone contains osteoinductive elements known as bone morphogenetic proteins (BMP). These BMP's are present within the compound structure of cortical bone and are present at a very low concentrations, e.g. 0.003%. The BMP's are present in higher concentrations in cancellous bone. BMP's direct the differentiation of pluripotential mesenchymal cells into osteoprogenitor cells which form osteoblasts. The ability of freeze dried demineralized bone to facilitate this bone induction principle using BMP present in the bone is well known in the art. However, the amount of BMP varies in the bone depending on the age of the bone donor and the bone processing. Based upon the work of Marshall Urist as shown in U.S. Pat. No. 4,294,753, issued Oct. 13, 1981 the proper demineralization of cortical bone will expose the BMP and present these osteoinductive factors to the surface of the demineralized material rendering it significantly more osteoinductive. The removal of the bone mineral leaves exposed portions of collagen fibers allowing the addition of BMP's and other desirable additives to be introduced to the demineralized outer treated surface of the bone structure and thereby enhances the healing rate of the cortical bone in surgical procedures. In cancellous bone which is not as dense as cortical bone, naturally occurring BMP's are exposed, rendering the entire structure with biological properties similar to full demineralized bone (DBM).

It is also possible to add one or more rhBMP's to the bone by soaking and being able to use a significantly lower concentration of the rare and expensive recombinant human BMP to achieve the same acceleration of biointegration. The addition of other useful treatment agents such as vitamins, hormones, antibiotics, antiviral and other therapeutic agents could also be added to the bone.

Any number of medically useful substances can be incorporated in the implant by adding the substances to the assembly. Such substances include collagen and insoluble collagen derivatives, hydroxyapatite and soluble solids and/ or liquids dissolved therein. Also included are antiviricides such as those effective against HIV and hepatitis; antimicrobial and/or antibiotics such as erythromycin, bacitracin, neomycin, penicillin, polymyxin B, tetracycline, viomycin, chloromycetin and streptomycin, cefazolin, ampicillin, azactam, tobramycin, clindamycin, gentamycin and silver salts. It is also envisioned that amino acids, peptides, vitamins, co-factors for protein synthesis; hormones; endocrine tissue or tissue fragments;

synthesizers; enzymes such as collagenase, peptidases, oxidases; polymer cellpl scaffolds with parenchymal cells; angiogenic drugs and polymeric carriers containing such drugs; collagen lattices; biocompatible surface active agents, antigenic agents; cytoskeletal agents; cartilage fragments, living cells and cell elements such red blood cells, white blood cells, platelets, blood plasma, pluripotential cells, chondrocytes, bone marrow cells, mesenchymal stem cells, osteoblasts, osteoclasts and fibroblasts, epithelial cells and endothelial cells present as a concentration of $10^5$ and $10^6$ per cc of a carrier, natural extracts, tissue transplants, bioadhesives, transforming growth factor (TGF-beta), insulin-like growth factor (IGF-1); platlet derived growth factor (PDGF), fibroblast growth factor (FGF) (numbers 1–23), osteopontin, vascular endothelial growth factor (VEGF), growth hormones such as somatotropin, cellular attractants and attachment agents, blood elements; natural extracts, tissue transplants, bioadhesives, bone digestors; antitumor agents; fibronectin; cellular attractants and attachment agents; inmuuno-suppressants; permeation enhancers, e.g. fatty acid esters such as laureate, myristate and stearate monoesters of polyethylene glycol, enamine derivatives, alpha-keto aldehydes can be added to the composition.

While the present invention is described for use in the cervical spine, it is also suitable for use in the lumbar and/or thoracic spine. The implant can be provided in a variety of sizes, each size configured to be inserted between a specific pair of adjacent vertebrae. For example, the implant can be provided in selected dimensions to maintain disc height, correct lordosis, kyphosis or other spinal deformities.

The principles, preferred embodiments and modes of operation of the present invention have been described in the foregoing specification. However, the invention should not be construed as limited to the particular embodiments which have been described above. Instead, the embodiments described here should be regarded as illustrative rather than restrictive. Variations and changes may be made by others without departing from the scope of the present invention as defined by the following claims:

What is claimed is:

1. A sterile composite graft comprising:
a first cancellous bone component member and a second monolithic load bearing component member adapted to be mounted to said first cancellous bone component, said cancellous bone component member defining a front end surface and a rear end surface, an open channel cut into the interior of the cancellous bone component member from said front surface leading to said rear surface, said monolithic load bearing component member having a front portion with a flat rear surface, an integral cross bar member extending outward from said flat rear surface of said front portion to a planar inner surface of a rear portion, said cross bar member being configured to fit into said channel cut into said cancellous bone component member holding said first and second component members together in a mated relationship.

2. A sterile composite graft as claimed in claim 1 wherein said first member is constructed of allograft cancellous bone taken from a group of bones consisting of a cancellous patella, femoral head, long bone condyles and talus.

3. A sterile composite graft as claimed in claim 1 wherein said load bearing component member is cortical bone.

4. A sterile composite graft as claimed in claim 1 wherein said cancellous bone component member has trapezoidal configuration and said load bearing component member front portion has a cross section area which is greater than the cross section area of said load bearing component member rear portion.

5. A sterile composite graft as claimed in claim 1 wherein said cancellous bone component member is a block with a C shaped cross section.

6. A sterile composite graft as claimed in claim 1 wherein said load bearing component member is constructed of ceramic having a compression load over 1000 Newtons.

7. A sterile composite graft as claimed in claim 1 wherein said load bearing component member is constructed of bioabsorbable polymers capable of bearing a compression load over 1000 Newtons.

8. A sterile composite graft as claimed in claim 1 wherein said load bearing component member is constructed of cortical bone which is at least partially demineralized.

9. A sterile composite graft as claimed in claim 1 wherein said cancellous bone component member is constructed of allograft bone which is at least partially demineralized.

10. A sterile composite graft as claimed in claim 1 wherein said load bearing component member front portion and rear portion have top and bottom surfaces which are angled so that planes taken across the same will intersect and said cross bar extending from said front portion engaging said rear portion has a lesser height than said front portion and said rear portion.

11. A sterile composite graft as claimed in claim 1 wherein at least one of said graft component members includes an additive taken from a group of living cells and cell elements consisting of red blood cells, white blood cells, platelets, blood plasma, pluripotential cells, chondrocytes, bone marrow cells, mesenchymal stem cells, osteoblasts, osteoclasts and fibroblasts, epithelial cells and endothelial cells present as a concentration of $10^5$ and $10^6$ per cc of a carrier.

12. A sterile composite graft as claimed claim 1 wherein at least one of said graft components includes an additive taken from a group of growth factors consisting of transforming growth factor (TGF-beta), insulin-like growth factor (IGF-1); platelet derived growth factor (PDGF), fibroblast growth factor (FGF) (numbers 1–23), osteopontin, vascular endothelial growth factor (VEGF), growth hormones such as somatotropin cellular attractants and attachment agents.

13. A sterile composite graft as claimed claim 1 wherein at least one of said graft component members includes an additive taken from a group consisting of antimicrobial effective against HIV and hepatitis; antimicrobial and/or antibiotics such as erythromycin, bacitracin, neomycin, penicillin, polymyxin B, tetracycline, viomycin, chloromycetin and streptomycin, cefazolin, ampicillin, azactam, tobramycin, clindamycin, gentamycin and silver salts.

14. A sterile composite graft as claimed in claim 1 including at least one pin mounted in both said cancellous bone component member and said load bearing component member.

15. A sterile composite graft as claimed in claim 1 wherein said component members define bores which are axially aligned when the component members are mated together.

16. A sterile composite graft as claimed in claim 15 wherein at least one of said bores is a blind bore.

17. A sterile composite graft comprising:
a cancellous bone component member and a monolithic load bearing component member matable with said cancellous component member, said cancellous bone component member defining a planar front surface and a planar rear surface with a channel extending between said planar front and rear surfaces into the interior of the cancellous bone component member, said monolithic load bearing component member having a modified I beam construction with a front portion, a cross bar secured to a rear surface of said front portion and a planar inner surface of a rear portion, said cross bar being configured to fit into said channel holding said component members together in a mated relationship.

18. A sterile composite graft as claimed in claim 17 wherein said component members define bores which are axially aligned when the component members are mated together.

19. A sterile composite graft as claimed in claim 18 wherein at least one of said bores is a blind bore.

20. A sterile composite graft as claimed in claim 18 wherein pins are mounted in said axially aligned bores, said pins extending across an intersection between said first cancellous bone component number and said second load bearing component member.

21. A sterile composite graft as claimed in claim 17 wherein said cancellous bone component member has a trapezoidal configuration.

22. A sterile composite graft as claimed in claim 21 wherein said cancellous bone component member has a "C" shaped cross section.

23. A sterile composite graft as claimed in claim 17 wherein said load bearing component member rear portion defines a curved outer proximal surface and a planar distal surface and said cross bar is integrally formed with said rear portion and extends away from said rear portion to engage said front portion, said front portion defining a planar proximal surface and a planar distal surface.

24. A sterile composite graft as claimed in claim 23 wherein said rear portion and said front portion have top and bottom planar surfaces, the planes of which form an angle.

25. A sterile composite graft as claimed in claim 24 wherein said angle ranges from 3° to 5°.

26. A sterile composite graft as claimed in claim 23 wherein said front portion has rounded edges leading to said distal planar surface.

27. A sterile composite graft as claimed in claim 17 wherein said rear portion and said front portion each form at least one planar surface forming a plane which is angled.

28. A sterile composite graft as claimed in claim 17 wherein said cross bar is rectangularly shaped.

29. A sterile composite graft as claimed in claim 17 wherein said load bearing component member is constructed of allograft cortical bone.

30. A sterile composite graft comprising:
a cancellous bone component member and a monolithic cortical bone component member having spaced front and rear portions which are connected by a support bar, said cancellous bone component member having a trapezoidal shape and a channel cut into the interior of the cancellous bone component member, said cortical bone component member front portion defining a flat rear wall surface which abuts said cancellous bone component member, an integral support bar extending from said flat surface of said front portion to a rear portion defining a flat inner surface which also abuts said cancellous bone component member, said integral support bar being configured to fit into said channel holding said cancellous and cortical bone component members together.

31. A sterile composite graft as claimed in claim 30 wherein at least one of said graft components include an additive taken from a group of living cells and cell elements consisting of red blood cells, white blood cells, platelets, blood plasma, pluripotential cells, chondrocytes, bone marrow cells, mesenchymal stem cells, osteoblasts, osteoclasts and fibroblasts, epithelial cells and endothelial cells present on a concentration of $10^5$ and $10^6$ per cc of a carrier.

32. A sterile composite graft as claimed in claim 30 wherein said component members define bores which are axially aligned when the component members are mated together.

33. A sterile composite graft as claimed in claim 32 wherein at least one of said bores is a blind bore.

34. A sterile composite graft as claimed in claim 30 wherein a pin is mounted in each of said axially aligned bores, said pin extending across an intersection between said first cancellous bone component number and said second load bearing component member.

35. A sterile composite graft as claimed in claim 30 wherein said bone block includes an additive taken from a group consisting of mesenchymal stem cells, natural extracts, tissue transplants, bioadhesives, transforming growth factor (TGF-beta), insulin-like growth factor (IGF-1), platelet derived growth factor fibroblast GF, osteopontin VEGF, blood elements.

36. A sterile composite graft as claimed in claim 30 wherein said cancellous bone component member has a C shaped cross section.

37. A sterile composite bone graft as claimed in claim 30 wherein said cancellous bone component member has side walls tapered at an angle ranging from about 100° to about 110°.

38. A sterile composite bone graft as claimed in claim 30 wherein said eortical bone component member has a curved end surface.

39. A sterile composite bone graft as claimed in claim 30 wherein said cortical bone component member has at least one inclined planar surface.

40. A sterile composite bone graft as claimed in claim 39 wherein said inclined planar surface is angled between a range of 3° to 5°.

41. A sterile composite bone graft as claimed in claim 30 wherein said support bar has a planar upper surface.

42. A sterile composite graft as claimed in claim 30 wherein said cancellous bone component member has an inclined planar top surface and an inclined planar bottom surface.

43. A sterile composite bone graft as claimed in claim 30 wherein said cortical bone component member has an inclined planar top and bottom surface.

44. A sterile composite bone graft for use in implants comprising:

a monolithic load bearing member constructed of allograft cortical bone having a front portion with a rear planar surface and a rear portion with an inner planar face interconnected by a support bar extending between said planar surfaces to connect said front and rear portions, an allograft cancellous member defining inwardly tapered side walls, a flat proximal end surface and a flat distal end surface and an open channel cut into said cancellous member extending from said proximal end surface to said distal end surface configured to receive said support bar, said monolithic load bearing member and cancellous member being mated together with said support bar being mounted in said cancellous member channel, said front portion and rear portion of said cortical bone member having a height which is at least equal to a height of said cancellous member when the same is mated to said cortical member with the rear portion of said load bearing member having a smaller cross sectional area than the front portion.

45. A sterile composite graft as claimed in claim 44 wherein said load bearing and cancellous members define bores which are axially aligned when the members are mated together, said cancellous member defining at least one blind bore and pin means mounted in said axially aligned bores, said pin means extending across an intersection between said cancellous bone member and said load bearing member.

46. A sterile composite bone graft as claimed in claim 44 wherein said side walls are tapered at an angle ranging from about 100° to about 110°.

47. A sterile composite bone graft as claimed in claim 44 wherein at least one of said members includes an additive taken from a group consisting of living cells, cell elements, red blood cells, white blood cells, platelets, blood plasma, pluripotential cells, chondrocytes, bone marrow cells, mesenchymal stem cells, osteoblasts, osteoclasts and fibroblasts, epithelial cells and endothelial cells present on a concentration of $10^5$ and $10^6$ per cc of a carrier.

48. A sterile composite graft as claimed in claim 44 wherein at least one of said members includes an additive consisting of natural extracts, tissue transplants, bioadhesives, transforming growth factor (TGF-beta), insulin-like growth factor (IGF-1), platelet derived growth factor, fibroblast GF, osteopontin VEGF, blood elements.

49. A sterile composite graft as claimed in claim 44 wherein said rear portion and said front portion of said loading bearing member have top and bottom planar surfaces, the planes of which form an angle.

50. A sterile composite graft as claimed in claim 44 wherein said side walls are tapered at an angle ranging from 3° to 5°.

51. A sterile composite graft as claimed in claim 44 wherein said rear portion and said front portion of said load bearing member form at least one planar surface forming a plane which is angled with respect to a longitudinal central axis drawn through said load bearing member.

52. A sterile composite graft comprising:

a cancellous bone component member and a monolithic cortical bone component member with an I-beam configuration, said cancellous bone component member having a trapezoidal shape and a channel cut into the interior of the cancellous bone component, said monolithic cortical bone component member defining a flat inner surface which abuts said cancellous bone component member, a connected support bar extending from said flat surface to a rear section defining a flat inner surface which also abuts said cancellous bone component member, said support bar being configured to fit into said channel holding said cancellous and cortical bone component members together.

53. A sterile composite bone graft for use in implants comprising:

a monolithic load bearing member with an I-beam configuration constructed of allograft cortical bone defining a front portion with a rear planar surface, a support bar extending from said rear planar surface to connect with a planar inner surface of a rear portion, an allograft cancellous member defining inwardly tapered side walls, a flat proximal end surface and a flat distal end surface and a channel cut into said cancellous member extending from said proximal end surface to said distal end surface, said load bearing member and cancellous member being mated together with said support bar being mounted in said cancellous member channel, said front portion and rear portion of said load bearing member having a height which is at least equal to a height of said cancellous member when the cancellous member is mated to said load bearing member.

* * * * *